(12) United States Patent
Hudson et al.

(10) Patent No.: US 8,921,278 B2
(45) Date of Patent: Dec. 30, 2014

(54) METHOD FOR THE DISCOVERY OF HIGH-AFFINITY, HIGH SPECIFICITY OLIGONUCLEOTIDE AND DERIVATIZED OLIGONUCLEOTIDE SEQUENCES FOR TARGET RECOGNITION

(75) Inventors: Bruce S. Hudson, Syracuse, NY (US); Philip N. Borer, Chittenango, NY (US)

(73) Assignee: Syracuse University, Syracuse, NY (US)

( * ) Notice: Subject to any disclaimer, the term of this patent is extended or adjusted under 35 U.S.C. 154(b) by 1596 days.

(21) Appl. No.: 11/387,553

(22) Filed: Mar. 23, 2006

(65) Prior Publication Data

US 2006/0257900 A1 Nov. 16, 2006

Related U.S. Application Data

(60) Provisional application No. 60/664,457, filed on Mar. 24, 2005.

(51) Int. Cl.
*C40B 30/04* (2006.01)
*C12Q 1/68* (2006.01)
*C40B 30/00* (2006.01)
*G01N 33/53* (2006.01)

(52) U.S. Cl.
CPC .......... *G01N 33/5308* (2013.01); *C12Q 1/6837* (2013.01); *G01N 2333/44* (2013.01)
USPC ..................... 506/9; 435/6.1; 506/7

(58) Field of Classification Search
CPC .... C12Q 1/6811; C12Q 1/6837; C40B 30/00; C40B 30/04; G01N 33/5308
USPC ........................... 435/6.1; 506/7, 9
See application file for complete search history.

(56) References Cited

U.S. PATENT DOCUMENTS

| 5,475,096 | A | | 12/1995 | Gold et al. | |
|---|---|---|---|---|---|
| 5,496,938 | A | | 3/1996 | Gold et al. | |
| 5,670,637 | A | | 9/1997 | Gold et al. | |
| 5,786,462 | A | | 7/1998 | Schneider et al. | |
| 5,821,046 | A | * | 10/1998 | Karn et al. | 435/4 |
| 6,569,630 | B1 | | 5/2003 | Vivekanada et al. | |
| 2001/0049104 | A1 | * | 12/2001 | Stemmer et al. | 435/6 |
| 2003/0165837 | A1 | | 9/2003 | Boger | |

FOREIGN PATENT DOCUMENTS

WO WO 99/31276 6/1999

OTHER PUBLICATIONS

Usman et al (1992 Nucleic Acids Research 20:6695-6699).*
Ben-Asouli et al (2000 Nucleic Acids Research 28:1011-1018).*
Boiziau, et al. "DNA Aptamers Selected Against the HIV-1 *trans*-Activation-Responsive RNA Element Form RNA-DNA Kissing Complexes," *The Journal of Biological Chemistry*, vol. 274, No. 18, pp. 12730-12737, Apr. 30, 1999.
International Search Report dated Aug. 28, 2006.

* cited by examiner

*Primary Examiner* — Heather Calamita
*Assistant Examiner* — Kaijiang Zhang
(74) *Attorney, Agent, or Firm* — Knobbe, Martens, Olson & Bear LLP

(57) ABSTRACT

A method is disclosed to obtain oligonucleotide sequences with high affinity to target molecules. By design, the oligonucleotides have a defined primary and secondary structure. The affinity for binding to target species is classified or quantified by assay measurements using physical measurements rather than being based primarily on separations. Targets include but are not limited to proteins, polymers, biological membranes including cells and organelles and small molecules.

24 Claims, 2 Drawing Sheets

Combimer motifs for hairpin (a) and internal/bulge (b) loops. The apical loop in (b) has an organized structure that is not expected to participate in target binding.

Figure1. Combimer motifs for hairpin (a) and internal/bulge (b) loops. The apical loop in (b) has an organized structure that is not expected to participate in target binding.

METHOD FOR THE DISCOVERY OF HIGH-AFFINITY, HIGH SPECIFICITY OLIGONUCLEOTIDE AND DERIVATIZED OLIGONUCLEOTIDE SEQUENCES FOR TARGET RECOGNITION

CROSS-REFERENCE TO RELATED APPLICATIONS

This application claims the priority of provisional application No. 60/664,457 filed Mar. 24, 2005 which is incorporated herein by reference.

BACKGROUND OF THE INVENTION

1. Field of the Invention

A method of identifying useful nucleic acid ligands with high affinity for target species is described. The target species may be an organism, a protein or other biopolymer or a small molecule. The nucleic acid ligands are characterized by a pre-defined primary and secondary structure which is retained in the final product.

2. Description of the Related Art

Nucleic acid constructs have been shown to have apparent affinities and selectivities that rival or exceed complexes with antibodies (Jayasena, S. D. (1999) Clin Chem, 45, 1628-1650; Gold, L. (1995) J Biol Chem, 270, 13581-13584). In addition, nucleic acids have been found that have high affinity and specificity for molecules that are too small to be immunogenic (Jenison, R. D., Gill, S. C., Pardi, A. and Polisky, B. (1994) Science, 263, 1425-1429). Antibody-based receptors cannot be created for most nerve gas agents and many common environmental contaminants. A sensor based on nucleic acid technology avoids many of the problems associated with antibody-based receptors and is applicable to both biological and chemical agents of a wide variety. The well-established methodology for discovery of high-affinity nucleic acid species used in these technologies is often referred to as SELEX (Systematic Evolution of Ligands by Exponential Enrichment) (U.S. Pat. Nos. 5,475,096 & 5,760,637; Tuerk, C. and Gold, L. (1990) Science, 249, 505-510); or in vitro selection (Ellington, A. D. and Szostak, J. W. (1990) Nature, 346, 818-822). This method uses iterative cycles of selection, amplification and cloning to discover target sequences known as "aptamers".

SELEX is a process for discovering a DNA or RNA aptamer. This method begins with a solution of DNA molecules that are a mixture of $10^{13}$ to $10^{14}$ possible sequences that are a small and unknown subset of all possible sequences. These molecules have randomized, "variable" sequence regions that are usually 30-50 nucleotides (N30 or N50), but may be as large as 120 nucleotides in length or, in principle, larger. A starting pool with $10^{14}$ sequences contains only a tiny fraction of the diversity in such variable regions; for instance these pools contain only these fractions of all possible sequences: N30 (~$10^5$), N50 (~$10^{16}$), N120 (~$10^{58}$), The variable region is flanked by fixed regions used in the amplification step. The target for selection of a high affinity sequence is mixed with this collection of sequences and the sequences that bind to the target are separated from those that do not bind as strongly (partitioning). A crucial washing step separates the bound and unbound species. The selected sequences are then amplified using nucleic acid enzymes. This process is repeated with more stringent requirements for affinity. Each cycle of selection and amplification enriches the sequence pool with fewer and fewer sequences. After repeating this process 9-15 times, the final high-affinity sequence pool is then cloned and each clone is sequenced. Examination of similarities in the resulting sequences may suggest a common tight-binding core sequence.

SELEX is very cumbersome, is prone to errors and is expensive to automate. The repetitive enzymatic/purification steps are cumbersome and time-consuming, often taking about 1 month to complete. Multiplexing requires expensive robotic equipment with frequent human interaction. The resulting sequences are generally larger than the minimal tight-binding sequences and sometimes very much larger than the minimal tight-binding sequence. The resulting aptamers tend to be large (50-100 nucleotides) and sometimes lack a defined secondary structure which limits their utility. This occurrence may be addressed by carving away the non-essential regions of a full-length aptamer to home in on the minimal tight binding aptamer "core". This is accomplished by preparing constructs with residues removed from each end of the aptamer and assessing binding affinity. This leaves a core. Quite often, these core sequences (15-30 bases) that retain a high affinity for the target exist as unbranched stem-loops containing mismatches, internal loops, and apical hairpin loops.

This carving procedure was used to define core binding sequences in the aptamer for the HIV-1 nucleocapsid protein (Lochrie, M. A., Waugh, S., Pratt, D. G., Clever, J., Parslow, T. G. and Polisky, B. (1997) Nucleic Acids Res, 25, 2902-2910; Berglund, J. A., Charpentier, B. and Rosbash, M. (1997) Nucleic Acids Res, 25, 1042-1049) and many other proteins. It has also identified core sequences that bind tightly to small molecules, such as the anti-asthmatic drug, theophylline, and antibiotics such as tobramycin (Jiang, L. and Patel, D. J. (1998) Nat Struct Biol, 5, 769-774). Distinguishing the binding core by carving away the non-essential regions is a lengthy iterative process. It is also prone to errors. We have demonstrated this to be so for the NC-binding core sequences derived from aptamers (Lochrie, M. A., Waugh, S., Pratt, D. G., Clever, J., Parslow, T. G. and Polisky, B. (1997) Nucleic Acids Res, 25, 2902-2910; Berglund, J. A., Charpentier, B. and Rosbash, M. (1997) Nucleic Acids Res, 25, 1042-1049), which are all about twice as large as the minimal binding sequence and have led to aptamer cores that bind multiple NC proteins (Paoletti, A. C., McPike, M. P., Yule, R., Hudson, B. S. and Borer, P. N. submitted for publication). While the parent aptamer must contain a high affinity binding sequence, it must also present it in an appropriate secondary/tertiary structural context. The carving procedure, a necessary final step in converting the products of SELEX to usable form, can destroy the context and allow different modes of binding to operate.

A similar example emphasizes that aptamer cores are larger than minimal tight-binding sequences. An aptamer core sequence with high affinity for theophylline was determined by carving away non-essential residues (Jenison, R. D., Gill, S. C., Pardi, A. and Polisky, B. (1994) Science, 263, 1425-1429; Zimmermann, G. R., Jenison, R. D., Wick, C. L., Simorre, J. P. and Pardi, A. (1997) Nat Struct Biol, 4, 644-649). Anderson et. al. (Anderson, P. C. (2005) J. Am. Chem. Soc., 127 (15), 5290-5291, 2005) recently refined the core binding domain to a 13-mer hairpin loop structure with stem mismatches. The 13-mer displayed similar affinity and selectivity to the longer 33-mer aptamer discovered by SELEX (Jenison, R. D., Gill, S. C., Pardi, A. and Polisky, B. (1994) Science, 263, 1425-1429). This refinement relied on a 3D structure of the aptamer (Zimmermann, G. R., Jenison, R. D., Wick, C. L., Simorre, J. P. and Pardi, A. (1997) Nat Struct Biol, 4, 644-649), then performed molecular dynamics simulations after removing residues from the aptamer core that are likely to be non-essential for binding. The 13-mer preserved essential H-bonding and stacking characteristics of the 33-mer. It had a $K_d$~10 µM and discriminated against caffeine by a factor of 40 (caffeine differs from theophylline by a single methyl group).

Embodiments of the present invention address the technical problems discussed above. Embodiments of the present invention differ from the SELEX method in that species with known primary and secondary structure are used. Therefore, candidate molecules have a defined secondary structure. The particular molecules selected from a library of candidate molecules has a defined secondary structure. Furthermore, there is no need to sequence the nucleic acid at any step in the process. Embodiments of the present invention use physical methods of affinity determination. Enzymatic amplification steps are not needed and there is no need to separate species on the basis of their affinity. Non-nucleic acid components may be incorporated. The practice of embodiments of the invention provides information on the affinity of species of known sequence which are not the strongest binding and results in a sequence that constitutes a minimized binding unit. There is no need to carve out a minimal tight binding core from a larger sequence. Constructs produced according to embodiments of the invention, in contrast to SELEX, may be readily incorporated into a biological switch.

Methods to rapidly discover nucleic acid oligomers that have high affinity and high specificity for protein and cellular targets are described. The resulting structures can easily be incorporated into bistable molecular sensors, such as OrthoSwitches™ (OrthoSystems, Inc.). The development of nucleic acid-based "capture" technologies represents an opportunity, currently unmet, in the entire area of sensors including those for air, food and water quality control, in medical diagnostics and in drug discovery.

SUMMARY OF THE INVENTION

Embodiments of the invention are directed to methods of obtaining combimers that bind to a target at a desired binding affinity, which include one or more of the following steps.
(a) designing an oligonucleotide library which includes oligonucleotides or analogs thereof having known primary and secondary structure, each of which includes a constant region and an enumerated region having N enumerated base positions, wherein each enumerated base position includes one of X selected nucleotide bases, such that the oligonucleotide library includes up to $X^N$ different oligonucleotides or analogs thereof;
(b) synthesizing at least some of the oligonucleotides or analogs thereof of the oligonucleotide library;
(c) classifying or quantifying the binding affinity of each oligonucleotide or analog thereof for the target; and
(d) identifying combimers with the desired binding affinity from the library of oligonucleotides or analogs thereof.
The combimer of step (d) is a member of the oligonucleotide library of (a) which includes the known primary and secondary structure of step (a).

In preferred embodiments, the method includes the additional step of selecting oligonucleotides or analogs thereof having an optimal binding domain from the library based upon the known primary structure of the enumerated region of the identified combimer with desired binding affinity.

In preferred embodiments the method steps (a) through (d) are repeated with a larger enumerated region, N. Most preferably, N is increased by 1-4 nucleotides each time.

In preferred embodiments, the oligonucleotides are chemically synthesized although the oligonucleotides may be enzymatically synthesized in some embodiments.

In preferred embodiments, the oligonucleotides includes DNA, RNA, and combinations of both DNA and RNA in the same structure.

In preferred embodiments, the method includes the additional step of catenating one or more combimers to produce a species with the desired binding affinity.

In some preferred embodiments, the combiner is chemically modified.

In preferred embodiments, the enumerated region includes 2-40 nucleotides, more preferably 2-20 nucleotides, yet more preferably 2-10 nucleotides and in most preferred embodiments, 2-5 nucleotides.

In some preferred embodiments, the target is a protein. In some preferred embodiments, the target is an organism. In some preferred embodiments, the organism is a virus. In a most preferred embodiment, the organism is cryptosporidium or giardia.

In some preferred embodiments, the target is a small molecule selected from toxins, environmental pollutants, drugs, and environmental contaminants.

In some preferred embodiments, the enumerated regions of the combimers is determined for more than one target.

In preferred embodiments, the desired binding affinity is medium binding affinity of $10^{-6}$ M<Kd<$10^{-2}$ M. In some preferred embodiments, the desired binding affinity is high binding affinity of $10^{-9}$ M<Kd<$10^{-6}$ M.

Embodiments of the invention are directed to combimers produced by any of the methods described above. In preferred embodiments, the target for the combiner is a protein target. Preferred embodiments include sensor constructs which include combimers obtained as described above.

Preferred embodiments of the invention include a nucleotide which includes two or more explicit binding sites for a target as produced by catenation of two or more previously identified combiner sequences which may be on the same or different molecules. Preferably, the target is a protein, an organism or a small molecule.

Embodiments of the invention are directed to nucleotides capable of binding to an organism with medium binding affinity of $10^{-6}$ M<Kd<$10^{-2}$ M. In preferred embodiments, the organism is a water-borne pathogen selected from cryptosporium and giardia.

Embodiments of the invention are directed to nucleotides capable of binding to a non-proteinaceous small molecule target selected from toxins, environmental pollutants, drugs, and environmental contaminants with medium binding affinity of $10^{-6}$ M<Kd<$10^{-2}$ M.

In preferred embodiments, nucleotides according to embodiments of the invention include a defined secondary structure that may result by chance, and contrary to the design of the method, using the SELEX method at non-detectable level.

Embodiments of the invention are directed to oligonucleotide libraries which include combimers having known primary and secondary structure each of which has a constant region and an enumerated region having N enumerated bases wherein each enumerated base position includes one of X selected nucleotide bases such that the oligonucleotide library comprises up to $X^N$ different combimers candidates.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIG. 2 shows a stem loop structure in which the symbols X, Y and Z represent standard bases G, C, A and T (for DNA).

DETAILED DESCRIPTION OF THE PREFERRED EMBODIMENT

Figure 1:
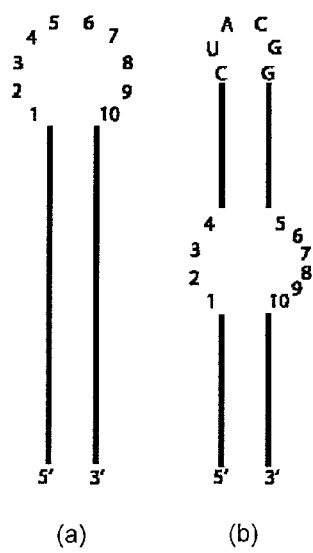
FIG. 1a shows combiner motifs for hairpin loops.
FIG. 1b shows combiner motifs for internal/bulge loops. The apical loop in (b) has an organized structure that is not expected to participate in target binding.

While the described embodiment represents the preferred embodiment of the present invention, it is to be understood that modifications will occur to those skilled in the art without departing from the spirit of the invention. The scope of the invention is therefore to be determined solely by the appended claims.

Embodiments of the invention relate to a method for the discovery of nucleic acid sequences that have high affinity for a specified target species. The described method is referred to as "Combigen" and the nucleic acid sequences which are discovered through the practice of the method are referred to as "combimers". The target species may include but are not limited to organisms, proteins and other biopolymers, and small molecules. The nucleic acid sequence has the additional property that it has a pre-defined secondary structure. By combining information on the binding affinity of a target for the nucleic acid sequence with information on binding of the target to related nucleic acid sequences, enhancement of target specificity is achieved. This method is particularly useful when the resulting Combigen species is to be used in a designed sensor construct for use in detection or high throughput screening such as those described in WO/2004/069850, which is incorporated herein by reference. This method becomes particularly efficient when a large number of target species are involved because the library of nucleic acid species can be reused for additional targets and because specificity information is cumulative.

In preferred embodiments of the described method, a structurally defined library of short DNA oligomers, whose affinity for a target species will be classified or determined directly, is prepared. This affinity measurement method can be efficiently automated for high speed screening.

Combigen is a method for the preparation of nucleic acids and nucleic acid derivatives and analogs that bind strongly to proteins, organisms, organelles and any other biological complexes or small molecules, such as toxins and environmental pollutants. The primary sequences of combimers resulting from Combigen include but are not limited to the "aptamers" resulting from SELEX but combimers differ from aptamers by having a defined secondary structure that is specified at the outset and retained in the final construct. In preferred embodiments, Combimers are nucleic acid derivatives and analogs thereof. In preferred embodiments, the proteins, organisms, organelles and any other biological complexes or small molecules that serve as the target ligands for Combimers do not normally bind to nucleic acids or nucleic acid derivatives under physiological conditions. That is, in preferred embodiments, the binding between the Combimer and its target ligand is not a naturally occurring binding reaction.

Combimers may or may not correspond to naturally occurring nucleotides. Without intending to be limited by theory, it is probable that all possible nucleic acid sequences shorter than a certain length have occurred naturally at one time or another. However, unless such sequences confer a selective advantage, they may be eliminated from biological systems. In this sense, all oligonucleotides shorter than 30 mers or possibly even 40-50 mers may be considered as naturally occurring.

The resulting combiner nucleic acid and extended composition constructs can be used for all of the applications for which antibodies are used in biotechnology and medical applications and for environmental, analytical and diagnostic purposes. Combimers may be used directly as therapeutic agents. For example, combimers may be utilized to bind to and inactivate a toxin or allergen. The use of combimers is in no way limited to these above areas of application. In fact, combimers may be utilized in applications which are unsuitable for the use of antibodies, such as small molecules which are too small to be antigenic.

Combimers may also be considered as lead compounds for further refinement in rational design or combinatorial processes. A few examples serve to illuminate the possibilities; but not limit the range of applications. (1) Segments of combimers with desirable binding properties for recognizing a specific target may be joined together to enhance selectivity and/or sensitivity. (2) Combimer-derived segments may be joined to designed or combinatorially derived segments to form structures such as OrthoSwitches™ with multiple stable conformational states. (3) Combimer-derived segments may be joined to molecules that include signaling or anchoring moieties (such as other refined combimers, antibodies, molecular beacons, or derivatized solid supports). (4) A large number of combimer-derived segments may be attached to an organized structure to produce nanostructures, nanomachines, or nanocircuits. Such organized structures include linear and branched polymers, polymeric surfaces, crystal lattices, filamentous bacteriophages, etc.

We refer to the sequences created by Combigen as "combimers," because (i) they present combining sequences to their targets in a manner analogous to the combining sequences of antibodies for antigens, and (ii) they can be identified from an exhaustive and directed search through a space of possible sequences.

Combimers, unlike antibodies, require no selection in animals or cell lines, have absolute uniformity from batch to batch, have shelf-lives of years in our hands, and they are easily adapted to our proprietary OrthoSwitch™ platform that responds rapidly to a binding event. The Combigen process by which Combimers are produced is direct synthesis and differs from SELEX which results in Aptamers. The class of species encompassed by the term Combimer includes species that cannot be prepared by SELEX and thus Combimers as a class differs from Aptamers as a class. Aptamers are a subset of Combimers. An important distinction is that Combimers may include ligand binding species with low and medium affinity for the target as well as high affinity binders. Such medium and low affinity binders are not obtainable using methods such as SELEX, or if they are obtained, would be washed away during the SELEX partitioning step so that they would not be retained and so would not be detected. Combimers and combimer-derived segments, unlike antibodies or aptamers, offer the possibility to (i) mix ribo, deoxyribo and modified nucleotides, (ii) incorporate peptides and mimetics, (iii) include enzyme cofactors, and organic natural products to enhance combining affinity and selectivity, and (iv) create combimer assemblies with multiple binding sequences that generate high selectivity and extremely low detection thresholds. For example, low and medium affinity Combimers may be combined to produce a high affinity high specificity oligonucleotide for target recognition.

Some proteins bind to specific nucleic acid sequences as part of their biological role. Often the nucleic acid binding region is a small loop sequence at the end of a double helical stem. Synthetic nucleic acid sequences can be prepared that bind to specific proteins with affinity that is comparable to that of antibodies. Methods for the selection of such sequences from random mixtures have been developed and described. These high affinity synthetic nucleic acid sequences have great potential in applications for which antibodies have been traditionally used. These advantages include the fact that such combining oligomers can be prepared with high affinity to targets that are too small to be antigenic. The ease, lower cost and automation of nucleic acid synthetic procedures in comparison to biosynthetic antibody production is another advantage. Nucleic acids are more stable than complex proteins like antibodies. Nucleic acid constructs can be derivatized so as to act as self-contained signaling groups.

What will be described here is a simple and efficient method to discover high affinity combining oligomeric nucleic acid structures (combimers). This method is more flexible than existing in vitro selection methods with respect to the chemical nature of the oligomer in question. Our procedure also affords a large increase in throughput compared to in vitro selection when a large number of target species are being investigated.

The central idea of Combigen is that specific, tight binding species of oligonucleotides can be found by
  (a) synthesis of a library of oligonucleotides with sequences that are largely or entirely known and with pre-defined secondary structures;
  (b) classification of the binding affinity of each of the members of that library to the target species;
  (c) expansion of the library to include larger oligonucleotide sequences;
  and/or
  (d) catenation of library species with moderate affinity to produce species with enhanced affinity and specificity.

In preferred embodiments, the members of the library will have defined primary and secondary structure. Secondary structures include but are not limited to hairpin, symmetric and asymmetric bulges, pseudoknots and internal-loop structures. The initial libraries may have either fully defined sequences or may include a variable sequence region which is fully or partially randomized. In preferred embodiments, some or all of the variable region is enumerated. That is, the base positions in the variable region are systematically varied to produce the desired sequence combinations. Any randomized sequences are specified in subsequent libraries to distinguish the optimal sequence(s). If more than one oligonucleotide species is identified with affinity, these can be built up into a larger structure with a variety of lengths and types of intervening units and each tested for affinity for the target.

DEFINITIONS

"Combigen" refers to the method disclosed herein for preparation of nucleic acids, nucleic acid derivatives and analogs that bind to a target.

"Combimers" refer to the nucleic acid constructs of the disclosed method that have binding affinity for a target. We define "combimers" to be high affinity combining sequences in a secondary structure context that ensures availability of the binding sequence for binding to the target. The combiner for a particular target is defined as a member of an oligonucleotide library which shows affinity for the target. By definition, the combiner includes the full secondary structure of the species identified as having affinity for a particular target.

"Combimer sequences" are defined as the sequence of the enumerated segment of the full combimer construct. In most preferred embodiments, this Combimer sequence segment is single stranded. There are, however, some cases in which double stranded nucleic acids are desired as the Combimer sequence. This is easily incorporated into the method using self-complementary sequences. This definition of "combimer sequences" includes aptamers, natural RNA combining sequences, any sequence that is accessible by direct solid-phase or enzyme-catalyzed synthesis. "Combimer-derived sequences" are defined as those for which the refinement of desirable properties is made by rational design or further combinatorial processes. Combimers may include DNA, RNA, DNA/RNA hybrids, and protein/DNA. Combimers may be chemically modified or may include chemically modified units in their sequence. Combimers may be catenated to produce high affinity ligand binding molecules with high specificity.

"Oligonucleotide" refers to a nucleotide sequence containing DNA, RNA or a combination. An oligonucleotide may have any number of nucleotides theoretically but preferably 2-200 nucleotides, more preferably 10-100 nucleotides, and yet more preferably 20-40 nucleotides. The oligonucleotide may be chemically or enzymatically modified.

"Target" means the putative binding partner for the combimers described herein and includes but is not limited to polymers, carbohydrates, polysaccharides, proteins, peptides, glycoproteins, hormones, receptors, antigens, antibodies, organisms, organelles, small molecules such as metabolites, transition state analogs, cofactors, inhibitors, drugs, dyes, nutrients, and growth factors and biological complexes or molecules.

"Combimer loop" refers to the loop region of a stem-loop secondary structure in a combiner molecule which preferably contains the ligand binding region.

"Enumerate" refers to a series of positions in an oligonucleotide sequence. Enumerated positions will have one of several different bases (generally G,A,T,C, or U) at each enumerated position. The enumerated positions are generally found in the Combimer loop.

"Designed sensor construct" means a construct that provides a signal upon binding of a ligand. For example, the signal may be the quenching of a fluorescent signal caused by a conformational change in the sensor construct upon binding a ligand.

Preparation of Oligonucleotide Libraries

The oligonucleotide libraries according to the invention may be prepared by chemical synthesis, enzymatically or a combination. The oligonucleotides may be DNA, RNA or combinations thereof. The length of the oligonucleotides is 2-200 nucleotides, more preferably, 10-100 nucleotides, more preferably, 10-50 nucleotides and most preferably 20-40 nucleotides.

The combiner sequence information is known by preparing one (or a few) sequences at a time. The nucleotide sequence of at least one region of the combiner is known and is systematically modified to create a family of sequence variants. The region of the nucleotide sequence which is varied is said to be enumerated. The construct may contain non-natural residues or, in general, any chemical entity that can be attached to a phosphoramidite or attached subsequent to solid-phase chain synthesis. High affinity sequences can also be connected to form a multidentate binding structure that provides high selectivity and detection thresholds. The array of sequences, each with a known chemical identity, in a combiner library can be built to span a large space of molecular diversity in a chip array. With an appropriate detection modality, such chips can be used to rapidly discover combimers for new proteins, organisms, or toxins.

In preferred embodiments, oligonucleotide library members preferably have, by design, regions of stable, defined secondary structure. An example of such a series of library entries will be the stem loop structures of the type shown in FIG. 1a in which a stable double helix structure has a terminal loop. The nucleotides of the terminal loop are enumerated 1-10 in FIG. 1a. A similar structure can be designed around a stem defect—an internal or bulge loop as shown in FIG. 1b. Two to twenty or more nucleotides could comprise the combiner loops. In preferred embodiments, tight-binding sequences can be found in loops of 4-16 nucleotides, and more preferably 6-12 nucleotides.

Combigen differs from prior art methods in that it is not necessary to partially randomize the binding region of each sequence. Rather, the sequence is enumerated as shown in FIG. 1a. That is, in preferred embodiments, the sequence of the variable region is methodically incremented to produce individual sequences with all possible variations. For example, if the variable region contained two nucleotides, 16 different oligonucleotides would be synthesized to cover all possible combinations. Once all possible variations for the first two nucleotides are prepared, the variable region can be expanded to 3-10 nucleotides and larger. At 10 nucleotides there are just over a million individual species (1,048,576). Thus, while over a million oligonucleotides may be synthesized for a loop of 10 nucleotides, the advantage to the disclosed method is that these sequences need be prepared only once. In preferred embodiments, the size of the variable loop is from 2 to 20 nucleotides, more preferably from 4 to 16 nucleotides, yet more preferably 6 to 12 nucleotides.

Measurement of Binding Affinity: Combigen Library Selection

Binding affinity is determined between the sequences from the oligonucleotide library and the target moiety and is measured quantitatively or classified either as high (too high to quantify accurately) or low (to low to quantify accurately). Generally, the stoichiometry of the binding for a particular target is also determined from the binding affinity assay. The Combigen method detects binding of the target molecule to the oligonucleotide trial sequence. As each oligonucleotide has been separately synthesized, it is not necessary to separate a mixture of oligonucleotides from each other. Each oligonucleotide preparation consists of either a unique or a relatively few chemical species and the binding assays can be carried out with high concentrations in very small volumes. In preferred embodiments, the individual oligonucleotides are present in an isolated, purified form, most preferably in an aqueous solution. Preferably, each oligonucleotide is present in an aqueous solution in concentrated form. Because of the high concentration of each sequence, binding affinity may be quantified even when the binding affinity is relatively low. Preferably, the concentration of the individual oligonucleotides is $10^{-3}$ to $10^{-12}$ M, more preferably $10^{-6}$ to $10^{-9}$ M. Once binding is observed, the oligonucleotide can be diluted to the point where a substantial fraction is no longer bound to the target so as to determine the binding constant. In preferred embodiments, affinities corresponding to dissociation constants on the order of $K_d$=100 nM or smaller are of interest where picomol amounts are adequate for multiple assays.

Binding affinity may be measured by any means known in the art. For some targets that are enzymes binding to the active site is detected using the enzymatic reaction that is catalyzed by that enzyme. In some embodiments, the oligonucleotide library may be arrayed on a solid support. In some embodiments, binding to the immobilized oligonucleotides is measured using a target tagged with a label such as a fluorescent probe. Alternatively, the binding of the target to the oligonucleotides on the solid support could be measured using a labeled antibody to the target. In many applications it is only necessary to classify the binding affinity into several categories ranging from high affinity to very low.

Although any binding assay may be used, a generally useful method to quantify binding is fluorescence polarization which is well-known in the art. Briefly, a fluorescent derivative of an oligonucleotide library member is prepared by well known methods or obtained from commercial sources. The fluorescence polarization of the oligonucleotide trial sequence is determined by measurement of the fluorescence intensity with two different polarization directions. The degree of polarization is a measure of the rapidity with which the fluorescent molecule tumbles in solution during the lifetime of the excited electronic state of the fluorophore. Rapid tumbling means low polarization. For the free oligonucleotide, the polarization is near zero. Upon binding, tumbling is inhibited and polarization increases. In preferred embodiments, measurements of the binding of target molecules to the members of the oligonucleotide library are performed with an automated device for measurement of fluorescence polarization.

Information from the affinity binding assays is used to build in an optimal binding site for one or more preferred oligonucleotide library members. The highest affinity sequence in the binding profile is selected as the potential combiner. For example, for an oligonucleotide sequence containing the subsequence, -GGab- (where a and b are enumerated), the second residue, G, is varied as -GXab- where X is a mixture of all four bases. Then each of the 16 cases of this (all possible a and b pairs one at a time) are tested on the MIXTURE sample -GXab- in which all four possible bases at the second position (X) are present at the same time. In order to illustrate, it might be found that "a" can be anything but "b" has to be G to get tight binding. It also turns out that "X" has to be G. But every sample has G in ¼ of its cases so every sample with b=G shows binding. The next step would be to make -GaYG- where the last position is always G, Y is any one of the bases (it apparently does not matter) and a is enumerated G, C, A, U. The "a" position, which corresponds to the previous "X" position which was randomized, is now enumerated to determine the optimal base for that position. That is 4 samples. There were 16 samples in the original -GXab- case so this is a total of 16+4 samples. If all of the Gabc cases were examined one at a time there would have been 4×4×4=64 samples. If the number of randomized bases is increased, then the concentration of each specific sequence is reduced by the number of possible combinations. Also, when an affinity for any one of the original -GXab- cases (each a mixture of four possibilities) is measured, you do not know if the binding indicates that all four sequences have moderate binding affinity or one of the four has high affinity. This can be determined with a series of affinity measurements on the mixture as a function of target concentration in a subsequent step; If only one of the four (or ¹⁄₁₆ or ¹⁄₆₄, etc.) cases has high affinity, then the measured effect used for affinity measurement (fluorescence polarization, counts bound to a filter) becomes reduced accordingly.

Note that the above-described method does not use enzymatic amplification so it is not necessary to include a conserved region for purposes of amplification. In preferred embodiments, the secondary structure is specified and largely fixed and the binding affinity is quantified directly.

In some embodiments, specificity is further established by measuring the binding of a combiner for one target to other targets that are considered to be important cross reactants.

Binding affinities may be classified or quantified for a single target or multiple target species. In preferred embodiments, binding of the oligonucleotide library members is classified or quantified for multiple targets.

Identification of Library Members with Optimal Binding Site

By combining the information on the binding affinities of library members, information on an optimal binding site cam be compiled. In one embodiment of this methodology, all of the $4^n$ specific sequences of an n-mer apical loop similar to FIG. 1a are prepared and constitute the library. A parallel library consists of internal-loop structures similar to that in FIG. 1b with specific sequences on the left (L) and right (R) sides; in the example shown L+R can range from 1 to 10 nucleotides.

In order to identify combimers for specific targets with greater efficiency one can adopt another version of the above procedure. In this embodiment of the method the 10-mer loop of FIG. 1a is allowed to have some variation. For example, positions 1, 2, 3 and 8, 9, 10 may be specifically enumerated but, for each flanking sequence, the central unit, 4,5,6,7, is constructed so that all possibilities occur in a mixture. If binding is found for some specific (1-3)/(8-10) sequences, then positions 4 and 7 could be specified by further synthesis and probing with the target. While this approach is efficient at finding combimers for one or a few targets, it is more efficient to use explicit, fully enumerated combiner libraries when the number of targets becomes larger.

The essence of the Combigen method is that defined sequences are bound to targets and affinities for that target are accurately classified or quantified. This information is then used either directly or with subsequent steps to construct high affinity, high specificity binding species.

These and other features of this invention will now be described with reference to the following example which is intended to illustrate and not to limit the invention.

EXAMPLES

Example

A Direct Method for Determination of High Affinity Nucleic Acid Binding Sequences for Cryptosporium, Giardia and Other Waterborne Pathogens (Combigen)

The detection of waterborne pathogenic agents in source or finished water is currently a laborious process involving expensive, unstable reagents and microscopic examination by a trained microscopist. The pathogens of primary concern are the encysted forms of cryptosporium and giardia. There are currently no sensor methods for detecting such organisms. The detection limits of interest to the Environmental Protection Agency (EPA) are on the order of 1 organism in 10 liters of water. This is an enormous technical challenge of immediate concern due to recent imposition of the EPA's LT2 rules for water treatment facilities. What is needed to meet this analytical challenge is a rapid way to detect pathogenic organisms that is suited to field use, using an inexpensive, environmentally stable reagent that has specific binding to these and other target organisms, whose presence can be detected with high sensitivity. The Combigen method described above is applied to solve this technical problem.

Combigen is used to determine nucleic acid sequences that have high affinity for targets with multiple identical sites on their surface, specifically waterborne pathogens including cryptosporidium and giardia. Unlike antibodies or aptamers, undesirable cross-reactions with non-target species can be minimized in a direct manner that will be described later.

Figure 2:
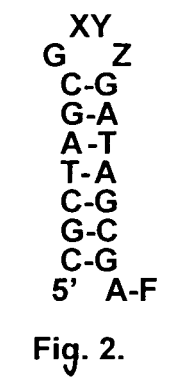

The Combigen method is based on the quantification of the binding affinity of a series of individual small nucleic acid sequences of known primary and secondary structure to the target of interest. An example of such a series is shown in FIG. 2 which is a stem loop structure in which the symbols X, Y and Z represent standard bases G, C, A and T (for DNA). The loop of the stem loop structure is sequentially substituted to produce each of the 64 possible individual sequences. The binding affinity and the number of binding sites per target organism is classified or quantified for each specific sequence in this series. This is a tetraloop sequence with G fixed as the first loop member and with a defined helical secondary structure. The symbol F at the 3' terminus represents a fluorescent group. A nucleic acid sequence that has a very high affinity and a very high specificity for the target organism is identified.

The goal is to detect one organism per liter ($10^{-24}$ M) and each organism has $10^6$ equivalent binding sites on its surface. This means that the concentration of binding sites is $10^{-18}$ M. If a signaling species has a dissociation constant $K_d$ of $10^{-18}$ M then when that species is present at a concentration of $10^{-18}$ M half of the sites will be occupied by signaling species. Flow detection methods with a small illuminated sample volume are used to detect signaling species. In the absence of an organism, the number of signaling species per 100 microliter sample volume is less than 100 at this concentration. This sets the background level. When one organism with a 100,000 signaling species bound to the organism drifts into the sample volume, the signal jumps by 1000-fold. Because of the large number of bound species bearing fluorophores on each target, the signal increase is narrowly distributed about its mean. This permits pulse-height discrimination methods for rejection of low level signals due to adventitious binding to non-target particles. The rare case of two organisms present in the sample volume at the same time results in a signal level above background that is twice as large. The illuminated sample volume is an important parameter in the design of a flow cell detector since it establishes the background signal level. A smaller sample volume as provided by laser illumination permits the use of higher concentrations of signaling species as would be needed for lower values of $K_d$. This is at the expense of a slower flow rate.

Oligonucleotide sequences are identified with $K_d \sim 10^{-18}$ M. After the initial screening, there are several strategies that are followed to achieve this end. One is to expand the sample size and search through a larger and larger space of sequences until a very high affinity sequence is found. This process is inefficient in practice if a single target species is the only one of interest but becomes competitive with "selection" methods if the number of target organisms is large. Increasing the number of enumerated bases (3 in the example above) increases the number of members of the library exponentially. In going from 3 to 10 enumerated bases the library size increases from $4^3=64$ to $4^{10}=1,048,576$. There is a substantial overhead cost in the preparation of these libraries. This cost can be recovered if a large number of target species are tested against each library. The overhead is only involved once.

When there are a large number of binding sites on the surface of the target organism, several units with low affinity are linked together. For example, if $K_d \sim 10^{-6}$ M for a particular stem loop, then linking three of these together in an optimal array results in $K_d \sim 10^{-18}$ M. Optimization of the linker size for cryptosporidium begins with linear arrangements in which the binding units, B, are linked in as B(L)B(L)B(L)B(L)B by linkers L. In preferred embodiments, the target molecules are multiple copies on the surface of the same organism resulting in very high affinity since the distinct target molecules on the surface are already bound to each other. In particular, virus particles have many copies of the same surface proteins. Two dimensional (cross linked) structures provide higher affinity and high specificity. More subtle situations are also imagined in which distinct non-competitive binding sequences, b1 and b2, both bind to the unit repeated on the surface of the organism. Then $b_1(l_{12})b_2$ becomes a high affinity unit for each site and B(L)B(L)B(L)B(L)B with $B=b_1(l_{12})b_2$ becomes a very high affinity binding unit for the target.

Linkage can also occur between distinct combimers that bind different proteins or other moieties on the surface of an organism, or distinct combimers that bind different parts of a single protein or other moiety. Then $b_i(l_{ij})b_j$ becomes a high affinity unit for each site and B(L)B(L)B(L)B(L)B with $B=b_i(l_{ij})b_j$ becomes a very high affinity binding unit for the target. This version of linkage applies to single proteins or other target moieties that present two or more, distinct binding sites where combiner binding to one site does not eliminate binding to the other site(s).

The choice of strategies depends on the outcome of the initial stage. Suppose that in the first round of screening no sequences are found that have significant affinity, then the library of specific sequences is expanded. As soon as structures with affinities of $K_d<10^{-6}$ M are found, these units are linked to provide higher affinity. If species with $K_d\approx10^{-4}$ M are those with the highest affinity for a given stem-loop size, then linkage of such units is initiated in parallel with examination of larger size stem loops. Additional target species are against the existing libraries.

The major features that differentiate this method from selection methods (such as SELEX) is that there is no need to sequence the nucleic acid at any step in the process since only one known sequence is present. Another feature that differentiates this method from SELEX and its relatives is that the quantitative determination of the binding affinity and number of binding sites for a specific sequence is the first step in the procedure, rather than the last step. As a result, when a particular library member is being tested for its affinity to a target, it will already be known what the affinity is of other members of this library for the targets previously investigated. While the giardia screening is performed, the prior cryptosporidium results are examined so that the giardia search can concentrate on those species that have low affinity for cryptosporidium and other targets. Specificity is built into the search. Similar information for “false” targets such as algae, various bacteria, etc. is incorporated into the choice of binding species. The library results obtained from Combigen become more and more useful in this respect as the number of target organisms increases. In a selection-based process, increasing the number of library members means adding an additional negative selection step early in the process.

The binding constant and number of sites for each target organism are classified or quantified using an equilibrium solution method based on fluorescence polarization. The nucleic acid library is labeled with a fluorescent species. The lifetime of the fluorescence of such species is on the order of 5 nanoseconds. The rotational diffusion for a stem loop structure of the required size is 2-3 ns. This leads to a low value of the anisotropy. Upon binding to the target species the rotational diffusion is inhibited and the degree of polarization of the emission increases. In this determination, the fluorescence signal is excited with polarized light and the degree of polarization of the fluorescence is measured. The relevant quantity is the difference in intensity for emitted light with polarization parallel and perpendicular to the excitation polarization direction. This is divided by the total intensity. A solution of molecules has a uniform orientation distribution with each molecule having a random orientation for its absorption transition dipole. Excitation with polarized light selectively excites (“photoselects”) a subset of the molecules in the sample. This selection is based on the degree of alignment of their absorption transition dipole with respect to the electric field of the excitation. This results in polarized emission unless rotational diffusion establishes a random distribution. Binding to a large species such as an organism inhibits rotational diffusion.

The degree of polarization is used to determine the fraction of bound (polarized emitter) and unbound (depolarized emitter) species as a function of the concentration of library member and target species. Measurements of the limiting values of the fully bound and fully unbound fluorescent library member are needed for this purpose. This is a standard method for such studies (Hill & Royer, Meth. Enzymol, 278, 390-416 (1997); Tretyachenko-Ladokhina et al., J. Mol. Biol. 316, 531-546 (2002)). Polarization has proven to be suited to $K_d$ values in the range of $10^{-12}$ to $10^{-3}$ M. Very high affinity requires alternative techniques as discussed below. Low affinity $K_d$ values are of special interest in the present context since high affinity will be achieved by catenation. In this respect this method differs from the usual implementation of selection processes which concentrate on the hypothetical high affinity binder in the complex pool. The present method has the advantage that it is not necessary to find the highest affinity binder in the pool. By catenating moderate affinity binding sites together, the functional equivalent of a single high affinity binding site is achieved. This strategy is particularly useful when the target contains multiple binding sites which are the same, as in a virus particle with multiple copies of the same surface protein.

An SLM T-format fluorimeter or comparable model is used for these studies. This fluorimeter uses two identical emission arms to permit simultaneous determination of the intensity for the two polarizations eliminating any effects from fluctuations in the light source. This permits determination of the anisotropy to a precision of 0.001. The full range of the anisotropy is 0 (depolarized) to ⅖=0.400 (fully polarized). The fraction of polarized (bound) species can thus be determined to better than 1%. Alternatively, polarization measurements may be carried out with plate reader devices designed for this purpose. Relatively high throughput is thus possible if screening large nucleic acid libraries is necessary. Plate reader polarization methods may be used to screen such libraries for tightly bound species that are subsequently investigated in more detail in the SLM fluorimeter.

The oligonucleotide libraries are chemically synthesized. Synthetic nucleic acid stem loops with a terminal fluorescein label are commercially available. Alternatively, a stem loop bearing a reactive species may be obtained from commercial sources to which a fluorophore is attached (Rusinova et al., Anal. Biochem. 308, 18-25 (2002)). The selected DNA structure can be cloned or PCR amplified permitting low-cost production in large amounts.

Competition Studies.

If more than one species is identified that has a $K_d<10^{-5}$ M, then competition studies will determine if they bind to the same site by challenging binding of one fluorescent species with one that does not have a fluorescent label. Species that bind to distinct sites are candidates for connection with short linker regions, the $B=b_1(l_{12})b_2$ or $b_i(l_{ij})b_j$ schemes mentioned above.

Linkage of Binding Units to Produce High Affinity Binding Species.

Linkage of binding species together to make high affinity species will involve synthesis of new DNA oligonucleotides that contain binding loops in a uniform unstructured background (e.g., poly T). These are made by direct synthesis or by ligation to oligo(T) pieces using a template. Once an optimized structure is identified it can be produced in quantity by enzymatic or cloning methods.

Fluorescent or Luminescent Signaling Groups on High Affinity Binding Candidates: Measurement of High Affinity Binding.

In the final constructs to be used for detection of waterborne pathogens, fluorophores are connected to the oligonucleotide sequences. These will provide the detection signal. These constructs are the functional equivalent of a fluorescent antibody with the significant advantages of reproducible and stable structure, very much higher environmental stability, higher affinity and control of cross reactivity. A major advantage of these Combigen selected nucleic acid species relative to an antibody is a lower cost by ca. 6-8 orders of magnitude permitting treatment of large volumes of water.

In preferred embodiments, the signal is measured in a flow cell system. Preferably, the sample volume is 10-1000 µl, more preferably, 50-500 µl, yet more preferably 80-200 In a most preferred embodiment, the sample volume is about 100 microliters.

In order to measure $K_d$, it is preferred to have roughly equal concentrations of free and bound species, generally in quantities on the order of $K_d$. In a most preferred embodiment, in order to detect fluorescent signals at low concentration and eliminate background noise from various sources, a flow cell with an illuminated volume and illumination intensity that are chosen so that the steady-state signal level is high enough to measure above background and the increase in signal when an organism moves into the flow cell is roughly equal to this steady-state signal level is used. This is the optimum condition for measurement of $K_d$.

Alternative Approach.

A library of the type of FIG. 2 with X=G (16 structures) bearing a fluorescein label is screened as described above. Rather than measuring binding to the entire oocyst, binding to surface proteins isolated from these organisms may be measured (Strong et al, Infect. Immun. 68, 4117-4134 (2000)). Polarization screening measurements is performed in triplicate at several concentrations. Multiple measurements of each intensity used to compute the polarization anisotropy are obtained and subjected to standard statistical evaluation. Favorable candidate sequences are evaluated in more detail to obtain binding constants and number of binding sites per oocyst from studies in which concentration is varied.

One advantage of the methods described above is the capability of assaying for a variety of waterborne pathogens in the same device with continuous monitoring providing warning of an outbreak prior to water distribution.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of obtaining combimers that bind to a target at a desired binding affinity, comprising the steps (a) through (d) in the following order:
    (a) designing an oligonucleotide library comprising oligonucleotides or analogs thereof having known primary and secondary structure, each of which comprises a constant region and a variable region comprising N enumerated base positions in a combimer loop region of the oligonucleotide or analog thereof, wherein each enumerated base position comprises one of X selected nucleotide bases, such that the oligonucleotide library comprises up to $X^N$ different oligonucleotides or analogs thereof, and wherein the nucleotide sequence is systematically modified to create a family of sequence variants, and wherein the region of the nucleotide sequence which is varied is said to be enumerated;
    (b) synthesizing at least some of the oligonucleotides or analogs thereof of the oligonucleotide library;
    (c) classifying or quantifying the binding affinity of the combimer loop region of each oligonucleotide or analog thereof for the target; and
    (d) identifying combimers with the desired binding affinity from the library of oligonucleotides or analogs thereof, wherein the combimer of step (d) is a member of the oligonucleotide library of (a) which comprises the known primary and secondary structure of step (a) and wherein N enumerated base positions comprises 2-40 nucleotides, and wherein the oligonucleotide library of (a) is reusable with multiple targets.

2. The method of claim 1, further comprising:
    selecting oligonucleotides or analogs thereof having an optimal binding domain from the library based upon the known primary structure of the combimer loop region of the identified combimer with desired binding affinity.

3. The method of claim 1, wherein the oligonucleotides are chemically synthesized.

4. The method of claim 1, wherein the oligonucleotides are enzymatically synthesized.

5. The method of claim 1, wherein the oligonucleotides comprise DNA.

6. The method of claim 1, wherein the oligonucleotides comprise RNA.

7. The method of claim 1, wherein the oligonucleotides comprise both DNA and RNA in the same structure.

8. The method of claim 1, further comprising catenating one or more combimers to produce a species with the desired binding affinity.

9. The method of claim 1, wherein the combimer is chemically modified.

10. The method of claim 1, wherein the enumerated region comprises 2-20 nucleotides.

11. The method of claim 10, wherein the enumerated region comprises 2-10 nucleotides.

12. The method of claim 11, wherein the enumerated region comprises 2-5 nucleotides.

13. The method of claim 1, wherein the target is a protein.

14. The method of claim 1, wherein the target is an organism.

15. The method of claim 14, wherein the organism is a virus.

16. The method of claim 14, wherein the organism is selected from the group consisting of cryptosporidium and giardia.

17. The method of claim 1, wherein the target is a small molecule selected from the group consisting of toxins, environmental pollutants, drugs, and environmental contaminants.

18. The method of claim 1, wherein binding affinity of the enumerated regions of the combimers is determined for more than one target.

19. The method of claim 1, wherein the desired binding affinity is medium binding affinity of $10^{-6}$ M<Kd<$10^{-2}$ M.

20. The method of claim 1, wherein the desired binding affinity is high binding affinity of $10^{-9}$ M<Kd<$10^{-6}$ M.

21. The method of claim 1, wherein the loop is a stem loop or internal loop.

22. The method of claim 1 wherein the variable region is fully enumerated.

23. The method of claim 1, further comprising repeating steps (b) through (d) with a larger enumerated region, N.

24. The method of claim 23, wherein N is increased by 1-4 nucleotides.

\* \* \* \* \*